US006196046B1

(12) United States Patent
Braig et al.

(10) Patent No.: US 6,196,046 B1
(45) Date of Patent: Mar. 6, 2001

(54) DEVICES AND METHODS FOR CALIBRATION OF A THERMAL GRADIENT SPECTROMETER

(75) Inventors: James R. Braig, Piedmont; Bernhard B. Sterling, Danville, both of CA (US); Daniel S. Goldberger, Boulder, CO (US); Joan C. Godfrey, Fremont, CA (US); Kamrava Azizi, San Ramon, CA (US); David J. Correia, Fremont, CA (US); Charles E. Kramer, Poway, CA (US)

(73) Assignee: Optiscan Biomedical Corporation, Alameda, CA (US)

( * ) Notice: Subject to any disclaimer, the term of this patent is extended or adjusted under 35 U.S.C. 154(b) by 0 days.

(21) Appl. No.: 09/382,273

(22) Filed: Aug. 25, 1999

(51) Int. Cl.[7] ............................................ G01N 1/00
(52) U.S. Cl. .................................................. 73/1.03
(58) Field of Search ............................ 73/1.01, 1.03; 250/252.1; 600/316; 356/243

(56) References Cited

U.S. PATENT DOCUMENTS 4,465,929 * 8/1984 Edgar .
5,068,536 * 11/1991 Rosenthal .
5,871,442 * 2/1999 Madarasz et al. .

* cited by examiner

Primary Examiner—Robert Raevis
(74) Attorney, Agent, or Firm—Lariviere, Grubman & Payne, LLP

(57) ABSTRACT

A calibration standard for calibrating a thermal gradient spectrometer. The calibration standard is a structure having a particular glucose concentration which a thermal gradient spectrometer reads for determining whether the spectrometer is in calibration. The structure of the calibration standard properly mimics the physiology of human tissue. A number of such standards, each containing a different concentration of glucose are provided in kit form with a thermal gradient spectrometer for use in calibrating the spectrometer. The spectrometer is provided with a display and internal circuitry for performing self-calibrating adjustments and a communications port for electronically coupling to a remote computer and database for supplying external calibration commands to said spectrometer.

20 Claims, 6 Drawing Sheets

| G-%mg/dl | Standard |
|---|---|
| 0 | 10 $G_1$ |
| 50 | 10 $G_2$ |
| 100 | 10 $G_3$ |
| 500 | 10 $G_4$ |
| 1000 | 10 $G_5$ |

DEVICES AND METHODS FOR CALIBRATION OF A THERMAL GRADIENT SPECTROMETER

TECHNICAL FIELD

The present invention relates to spectrometers used for the non-invasive generation and capture of thermal gradient spectra from human or animal tissue. More particularly, the present invention relates to devices and methods that calibrate spectrometers of the type that are used for the non-invasive generation and capture of thermal gradient spectra from human or animal tissue. Even more particularly, the present invention relates to calibration methods and devices that contain a base source of thermal gradient spectra associated with glucose to test and calibrate a spectrometer used for the non-invasive generation and capture of thermal gradient spectra from human or animal tissue.

BACKGROUND OF THE INVENTION

Millions of diabetics are force to draw blood daily to determine their blood sugar levels. To alleviate the constant discomfort of these individuals, substantial effort has been expanded in the search for a non-invasive apparatus and methodology to accurately determine blood glucose levels. Four patent applications, each assigned to Optiscan Biomedical Corporation of Alameda, Calif., have significantly advanced the state of the art of non-invasive blood glucose analysis The methodology taught in U.S. patent application Ser. No. 08/820,378 is performed by the apparatus taught in U.S. patent application Ser. No. 08/816,723, and each of these references is herewith incorporated by reference. While the methodology taught in the incorporated references presents a significant advance in non-invasive glucose metrology, there exists room for further improvements. One such improvement lies in the manner in which the data collected by the apparatus are manipulated. In the methodology taught in Ser. No. 08/820,378 a volts-to-watts radiometric calibration step is often required. To preclude this requirement, U.S. patent application Ser. No. 09/267,121 teaches a methodology that takes advantage of the fact that by inducing a temperature gradient, a difference parameter between the signal at a reference wavelength and the signal of an analyte absorption wavelength may be detected. The frequency or magnitude or phase difference of this parameter may be used to determine analyte concentration. A further object of the invention taught therein is to provide a method of inducing intermittent temperature modulation and using the frequency, magnitude, or phase differences caused by analyte absorbance to determine analyte concentration. This intermittent temperature may be periodic or a periodic. Another improvement concerns U.S. patent application Ser. No. 09/265,195 entitled: "Solid-state Non-invasive Infrared Absorption Spectrometer for the Generation and Capture of Thermal Gradient Spectra from Living Tissue" which teaches a method of inducing a temperature gradient and monitoring of radiation emitted from test samples. The complete teachings of U.S. patent application Ser. No. 09/267,121 and Ser. No. 09/265,195 are also herewith incorporated by reference.

As has been noted in Ser. No. 09/265,195, the non-invasive spectrometer require calibration to assure quality performance to the diabetic end user. While such calibration presents no particular difficulty in the laboratory environment, it will be appreciated that accurate calibration in the field presents some rather interesting challenges. The laboratory type standards are basically an aqueous solution of glucose, where the exact concentration of glucose is known. However, once this type of prior art standard solution leaves the laboratory it is subject to a wide variety of environment effects which can serve to degrade its accuracy. Such effects include, but are not limited to evaporation, contamination, fermentation, dilution, sundry photochemical effects, spillage, and the like. Given the need for extremely precise measurements afforded by the principles of the present invention, any degradation in accuracy is unacceptable. A further second problem lies in the fact that a prior art solution of glucose cannot properly mimic the physiology of human tissue. To applicants' knowledge there are no known standards available for use in calibrating a non-invasive spectrometer in the field that can overcome the foregoing problems associated with laboratory standards comprising aqueous solution of glucose.

Thus, a primary object of the present invention is to provide a calibration standard apparatus for use in calibrating a non-invasive spectrometer in the field.

A related object of the present invention is to provide a field calibration standard that overcomes the problems associated with prior art laboratory type of standards comprising aqueous solution of glucose.

An other object of the present invention is to provide a field calibration standard that properly mimic the physiology of human tissue.

Yet another object of the present invention is to provide a spectrometer apparatus that not only can perform non-invasive glucose level tests in humans, but that is adapted to receive the calibration standards and perform the thermal gradient calibration measurements.

BRIEF SUMMARY OF THE INVENTION

Accordingly, the foregoing object is accomplished by providing a calibration standard for calibrating a thermal gradient spectrometer. The standard comprises a structure having a particular glucose concentration which a thermal gradient spectrometer reads for determining whether the spectrometer is in calibration. The structure of the calibration standard properly mimics the physiology of human tissue. Human tissue, and most importantly human skin, is a layered structure. Accordingly, the principles of the present invention contemplate the use of layered polymeric standard structures which closely mimic human skin. A number of such standards, each containing a difference concentration of glucose, may be used.

One structure for such a standard includes a number of polymeric layers. The first layer, that which is placed in contact with the optical window of the spectrometer is intended to mimic the stratum corneum. The second layer mimics the epidermis. Standards are provided at a variety of glucose concentrations including concentrations consisting of 0% glucose; 50 mg/dL glucose (physiological hypoglycemia); 10 mg/dL glucose (physiological normal); 500 mg/dL glucose (physiological hyperglycemia); and 1000 mg/dL glucose (outside the physiological limits). The standards are packed in a hermetic container and treated to prolong shelf life and to retard microbial growth. Sterile standards are also within the scope of the present invention. The container, and the standards themselves are provided with imprinted data about the standard, including its glucose concentration. The labeling could be machine-readable, for example, using a bar code.

In use, a spectrometer is placed in a calibration mode, manually or automatically upon presentation of the standard thereto. The spectrometer then reads the encoded information from the standard, or as manually entered. The spectrometer then scans the standard. When complete, the instrument prompts for the next standard in the series. When all standards in the series have been scanned, the spectrometer post-processes the data. The instrument may then determine that it is within specification, and so notifies the operator. The instrument could also determine that it is out of specification and may perform an automatic adjustment. It will then notify the operator that the adjustment have been successfully accomplished. The instrument may also determine that it is out of specification and that it requires manual adjustment. The operator must be notified accordingly. In each of the above cases, operator notification may additionally require a network connection to a computer or remote database. Such network connection may provide not only a repository for calibration information for a number of instruments, but may serve to automatically calibrate the instrument from the remote location. In similar fashion, the network connection may also be utilized to retain a remote database of patient information, and for a repository of treatment options given a certain patient history and reading.

Other features of the present invention are disclosed or apparent in the section entitled: "DETAILED DESCRIPTION OF THE INVENTION".

BRIEF DESCRIPTION OF DRAWINGS

For fuller understanding of the present invention, reference is made to the accompanying drawing in the following Detailed Description of the Invention. In the drawings.

Figure 1:
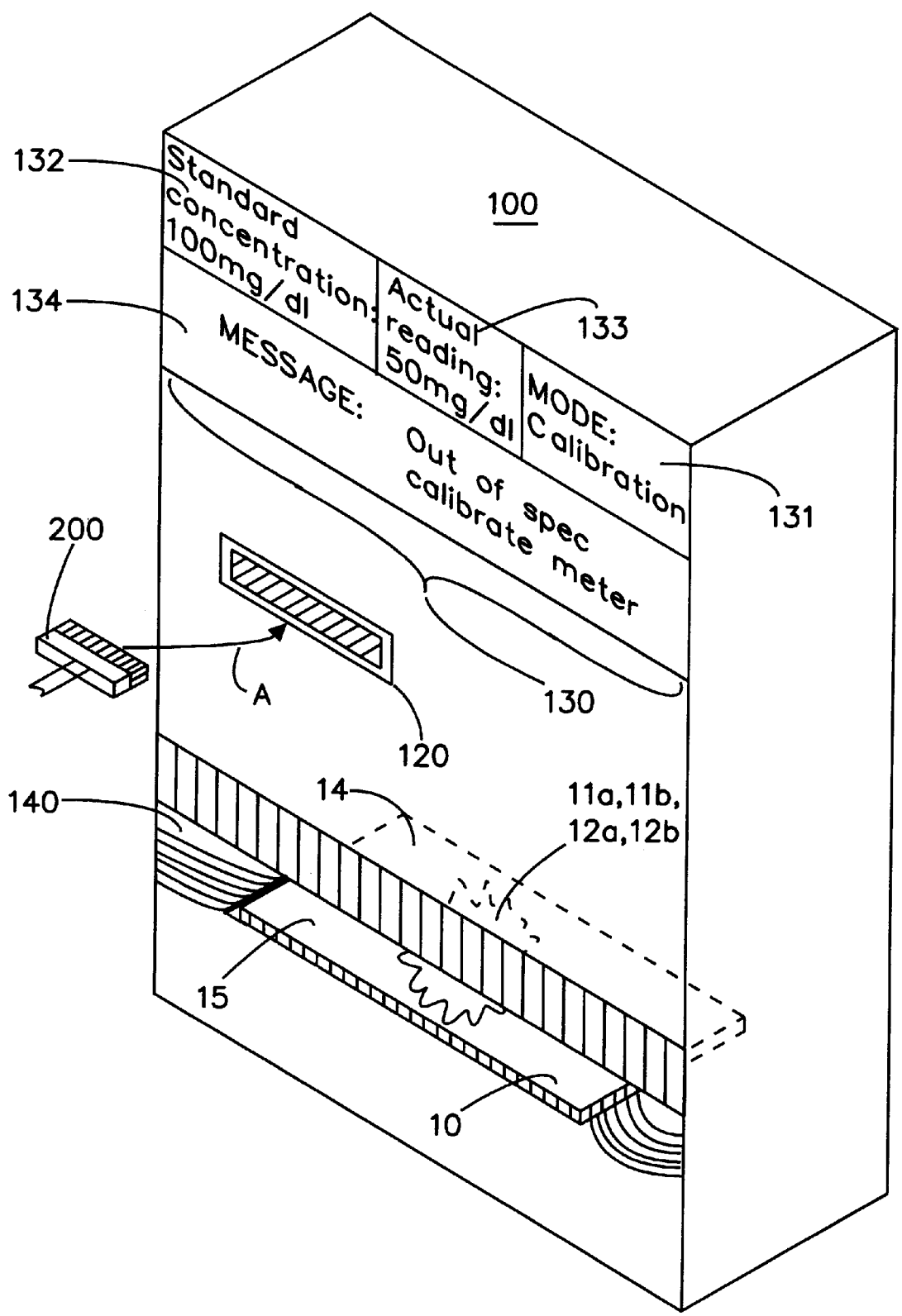
FIG. 1 is an embodiment of a thermal gradient spectrometer adapted for being calibrated using the calibration standard of the present invention.

Reference numbers refer to the same or equivalent parts of the invention throughout the several figures of the drawing.

DETAILED DESCRIPTION OF THE INVENTION

Referring to FIG. 1, and by example only, an embodiment of a thermal gradient spectrometer 100 is shown having a remote communications port 120, a display portion 130, and an input port 140 for receiving a calibration standard 10, in accordance with the present invention. Display portion 130 is shown having respective window areas 131 for mode of meter operation, 132 for displaying standard concentration value, 133 for displaying actual concentration readout, and 134 for displaying message of results and suggested action.

Figure 2:
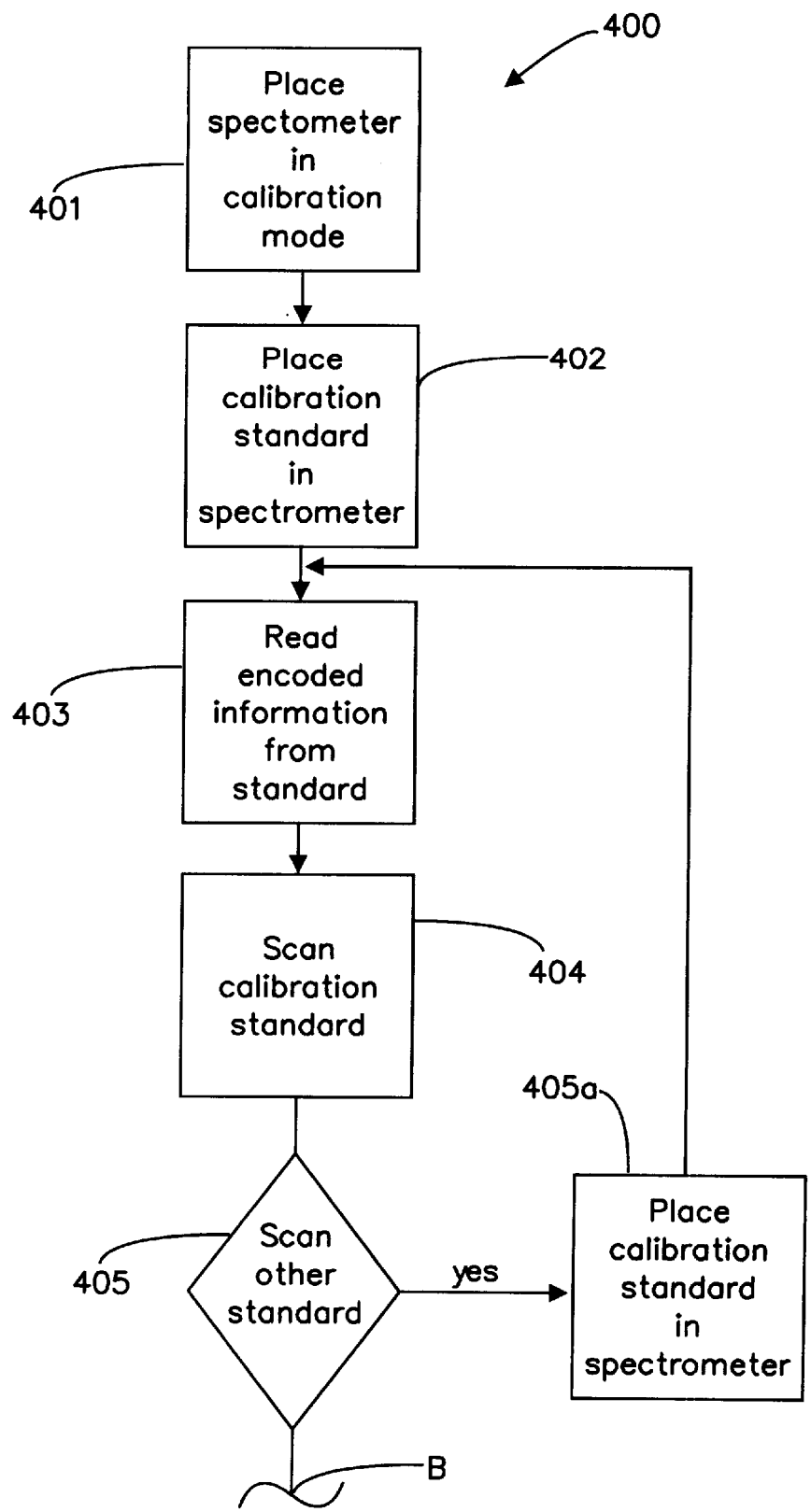
FIGS. 2 and 3 collectively show a flow chart methodology for calibrating a thermal gradient spectrometer using the glucose calibration standards of the present invention.
Figure 3:
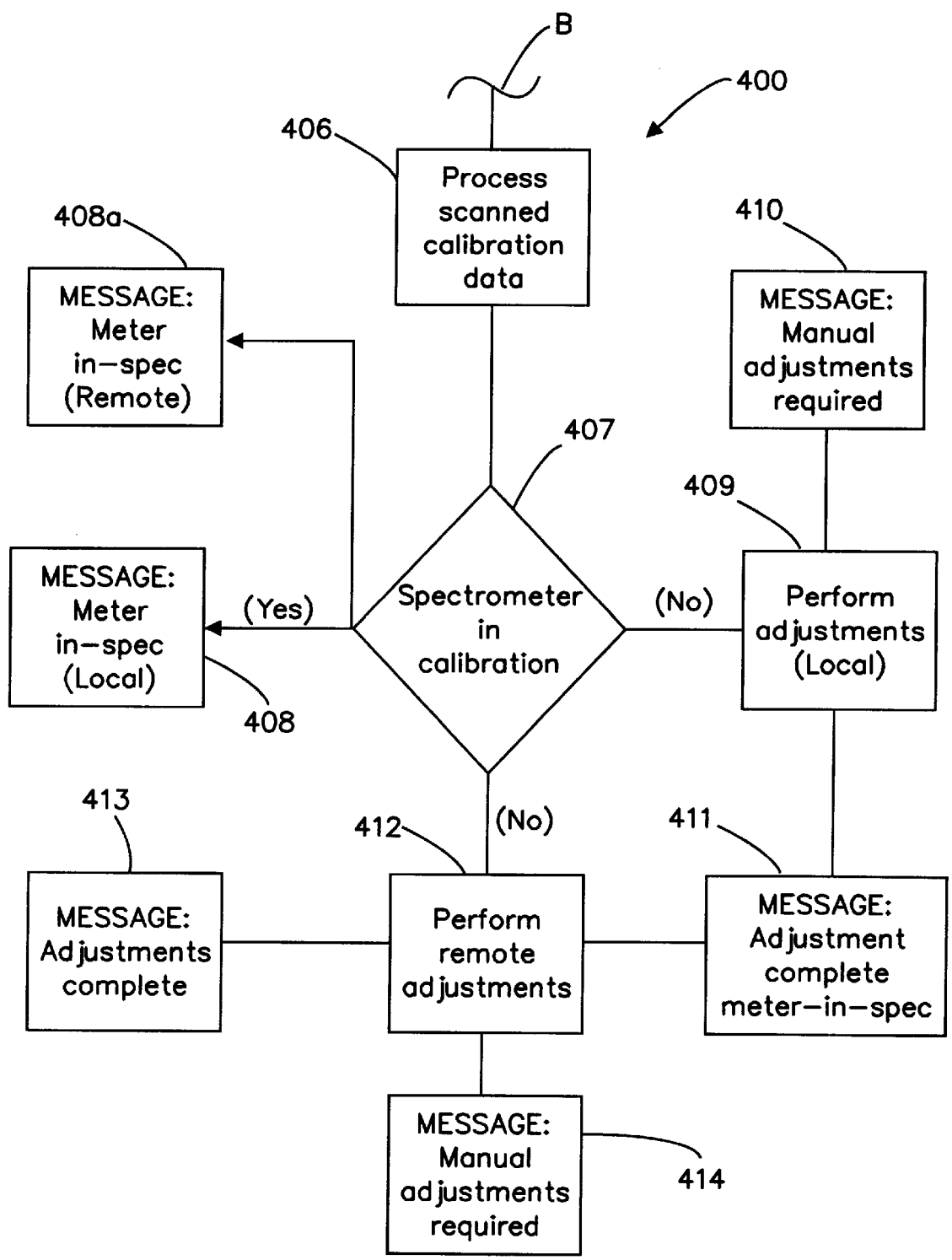
Figure 4:
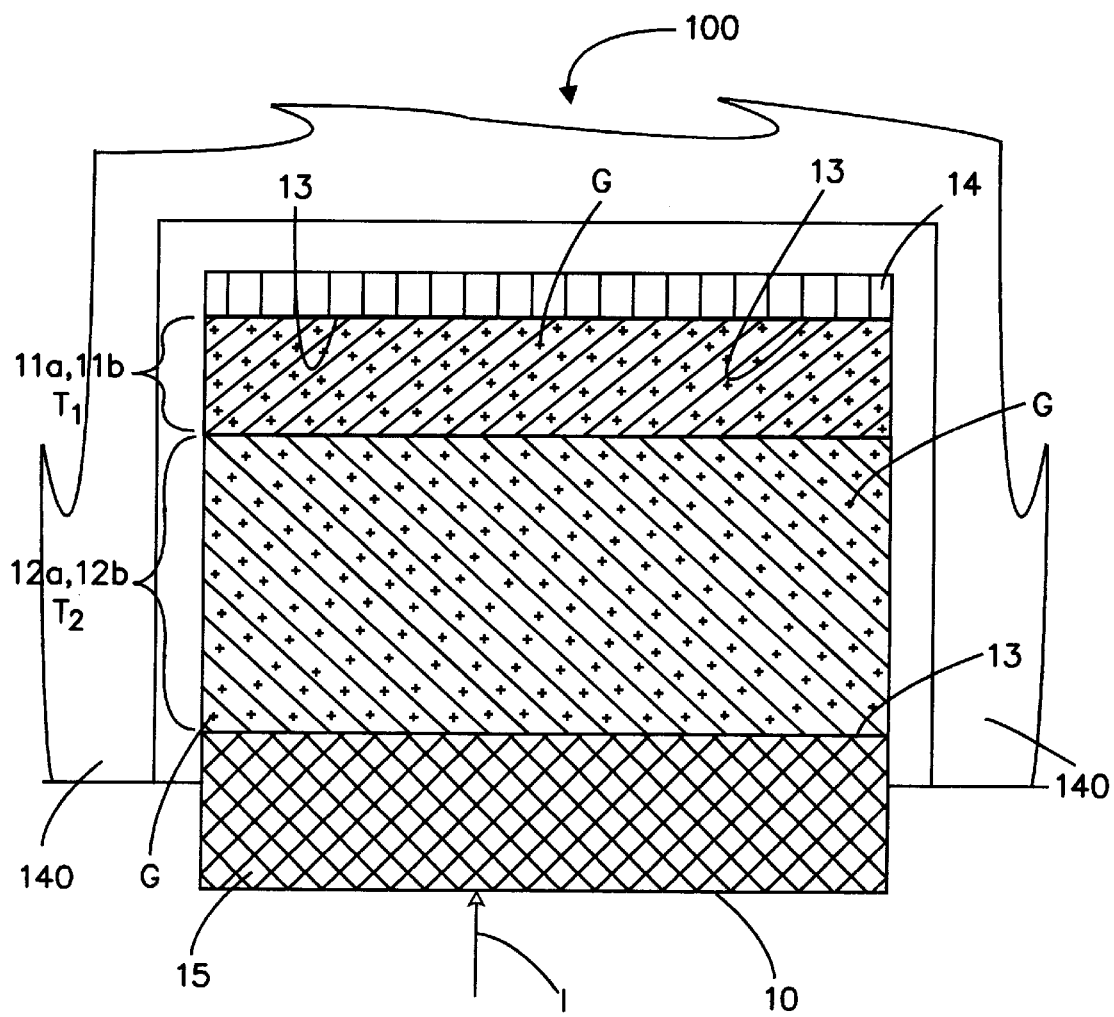
FIG. 4 is a fragmented cutaway of the spectrometer thermal window showing a calibration standard in place for being read by the spectrometer thermal gradient sensory elements.

Port 120 is shown with a network communicating means 200 for being inserted, as shown by arrow A, to primarily effect remote calibration of meter 100. Other functions may be provided via communication means 200, such as to effect a network connection to a computer or remote database. As indicated above, such network connection may provide not only a repository for calibration information for a number of instruments, but may serve to automatically calibrate the instrument from the remote location. In similar fashion, the network connection 200 may also be utilized to retain a remote database of patient information, and for a repository of treatment options given a certain history and reading. Input port 140, in combination with standard 10, essentially simulate the patient's skin that would normally be exposed to the spectrometer's thermal mass to effect thermal gradients. In fact, in the embodiment of standard 10 shown in FIG. 4, areas 11 and 12 comprise standard portions at two temperatures $t_1$ and $t_2$. As background information, the spectrometer's thermal mass window's function is threefold. One function is to cool the measurement "site", another to warm it, and the last is to efficiently collect and transmit the infrared energy to the collector and detector systems. Thus, as shown in FIG. 2 calibration process 400 comprises a step 401 of placing the spectrometer in calibration mode, as opposed to user mode, then a step 402 of placing standard 10 in port 140. At this point the spectrometer thermal mass window, generally shown as numeral 141, will perform these functions on standard 10. The operation of meter 100, as it performs these functions is the same as if being used on a human tissue, as described in U.S. patent application Ser. No. 09/265,195, incorporated herein by reference. As process 400 continues, and as indicated at steps 403 and 404, the leading end portion 14 of standard 10 is read and then the thermal gradient areas 11 and 12 are scanned. Spectrometer 100 is programmed to query the user at step 405 whether there are other standards to be scanned. If yes, the process continues to step 405a to repeat the data gathering function of steps 403 and 404. If not other standards are to be scanned, then the process continues to step 406, as shown in FIG. 3, connected by numeral B from FIG. 2. At steps 406 and 407, spectrometer 100 processes the data gathered and provides a user with the results of the calibration task and makes a determination of the action to be taken. If, by example, the results are that the meter is in calibration and within specifications, then at step 408 an "in-spec" message is displayed on display portion 134, or if being calibrated remotely at step 408a, an "in-spec" message displayed to an operator at a remote location. If the results are that the spectrometer is out of calibration and requires adjustments, then depending upon the availability of remote or local adjustment features on the spectrometer, either step 412 for remote adjustments are executed, or step 409 for local adjustments are executed. Assuming that step 409 is performed, then meter 100 will either display an "in spec" message on display portion 134, as indicated at step 411, or if out of specification, such that internal self-adjustments were not successful, then a message to perform manual adjustments is displayed on display portion 134, as indicated at step 410. If, by example, a remote calibration is desired, as indicated at step 412, then the results will either be a successful "adjustment complete" message displayed on display portion 134, as indicated at step 413, or results that the remote adjustment were not successful, resulting in a message on display portion 134 that manual adjustments are required, as indicated in step 414.

Figures 5, 6:
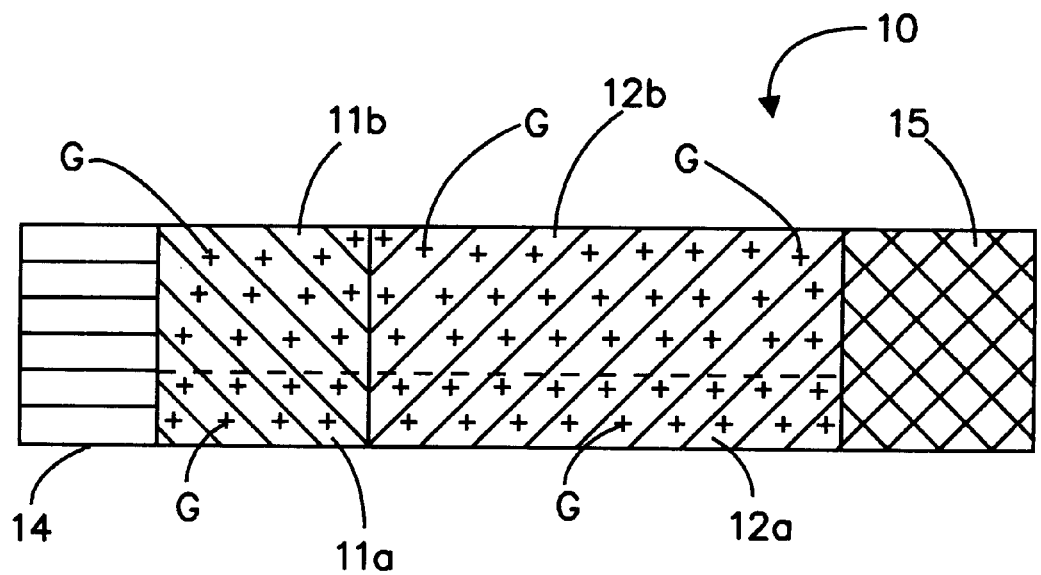
FIG. 5 is a table showing a list of calibration standards with glucose concentrations that span the glucose concentration spectrum of interest for calibration purposes.
FIG. 6 is an enlarged cross-section of a calibration standard apparatus having a leading end portion, a thermal gradient body portions laden with glucose, and a handling portion.
Figure 8:
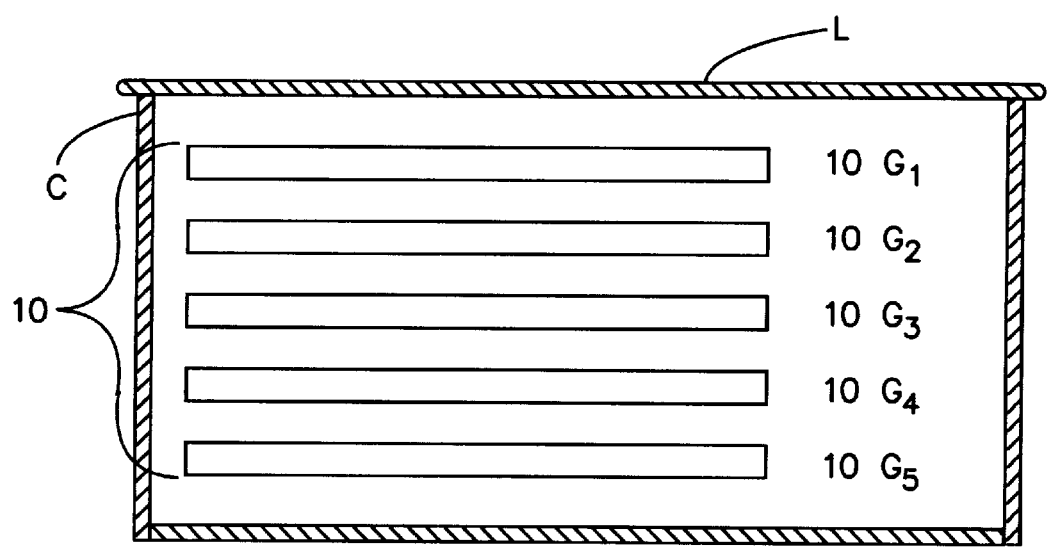
FIG. 8 a collection of calibration standards in a container and which are listed in the table shown in FIG. 5.

The preferred embodiment of the present invention contemplates the use of layered polymeric standard structures which closely mimic human skin. FIG. 4 and FIG. 6 show a layered polymeric standard structure 10 in accordance with the present invention. As best seen in cross-section in FIG. 6, standard 10 comprises a leading end portion 14, which will be the end of standard 10 to be inserted into port 140 of spectrometer 100, (as indicated by insertion arrow), a major standard portion comprising two layered human skin simulating portions (11a, 11b) and (12a, 12b), and a back-end handling portion 15. Major standard portion (11a, 11b) and (12a, 12b), are partitioned from leading end portion 14 and back end portion 15 by a partition 13, comprising material suitable to confine the glucose to the major standard portions (11a, 11b) and (12a, 12b). The first layer of standard 10, comprising portions 11a and 11b, are on the side of standard 10 that is placed in contact with the optical window of the spectrometer. Structure portions 11a and 12a are intended to mimic the stratum corneum. The second layer portions 11b and 12b of standard 10 are intended to mimic the epidermis. It should be understood that a number of such standards 10, each containing a different concentration of glucose G, may be used. This aspect of the invention is best seen by referring to FIGS. 5 and 8, showing standards $10G_1$, $10G_2$, $10G_3$, $10G_4$, and $10G_5$, containing 0%, 50, 100, 500, 1000 mg/dl of glucose, respectively.

Figure 7:
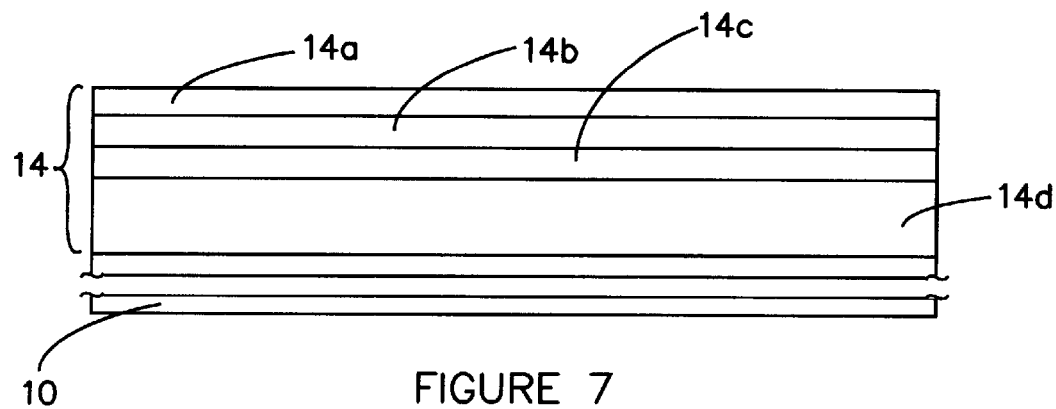
FIG. 7 is an enlarged view of the leading end portion showing a breakdown of the embedded coded information.

FIG. 7 shows an enlarged view of the leading end portion 14 showing a breakdown of the embedded coded information. By example, the leading end portion contains a bar code portion 14a, a resistor code 14b, a semiconductor memory device 14c such as a programmable read only memory (PROM), and a reserved space 14d for future code features.

Layered polymeric standard portion 11a, 12a, in accordance with the present invention, have the following properties:

Thickness=50 $\mu$m+/−20 $\mu$m;

Moisture content less than 20%;

No spectral features in the infrared band from 3–12 $\mu$m;

Thermal conductivity in the range of 0.21 to 0.26 watts/meter-° C., and

Specific heat in the range of 3578 to 3600 Joules/Kg-° C.

The second layer portions 11b, and 12b which mimic the epidermis and have the following properties:

Thickness=300 $\mu$m+/−50 $\mu$m;

Moisture content=80% +/−10%;

Glucose spectral features at 9.6 $\mu$m;

No other spectral features in the infrared band from 3–12 $\mu$m;

Thermal impedance in the range of 0.3 to 0.52 watts/meter-° C., and

Specific heat in the range of 3200 to 3400 Joules/Kg-° C.

As shown in FIG. 8, the standards $10G_1$, $10G_2$, $10G_3$, $10G_4$, and $10G_5$, are packed in a hermatic container C and treated to prolong shelf life and to retard microbial growth. Sterility may, or may not be desirable. The container C, should have information about the standards on a label, shown generally as label L. The data should reflect information on front end portion 14 about the contained standards, including the glucose concentration. The labeling could be machine-readable, for example, using a bar code.

To summarize process 400, the spectrometer is placed in a calibration mode, manually or automatically upon presentation of the standard thereto. The spectrometer then reads the encoded information from the standard, or as manually entered. The spectrometer then scans the standard. When complete, the instrument may prompt for the next standard in the series. When all standards in the series have been scanned, the spectrometer post-processes the data. The spectrometer then determines that it is within specification, and if so notifies the user locally, or an operator remotely. The spectrometer may, however, determine that it is out of specification and may perform an automatic adjustment. It will then notify the operator that the adjustments have been successfully accomplished. The instrument may determine that is out of specification and requires manual adjustment. The operator must be notified accordingly. As previously stated, in each of the above cases, operator notification may additionally require a network connection to a computer or remote database. Such network connection may provide not only a repository for calibration information for a number of instruments, but may serve to automatically calibrate the instrument from the remote location, as executed following process 400. In similar fashion, and not illustrated in the flow diagram for process 400, the network connection may also be utilized to retain a remote database of patient information, and for a repository of treatment options given a certain patient history and reading.

It will be appreciated that many modifications can be made to the calibration standard structure and spectrometer described above without departing from the spirit and scope of the invention. Various other advantages of the present invention will become apparent to those skilled in the art after having the benefit of studying the foregoing text and drawings, taken in conjunction with the following claims.

What is claimed is:

1. A calibration standard apparatus for use in calibrating a thermal gradient spectrometer, said apparatus comprising:

a layered polymeric standard having a structure that simulates human skin, said structure being flat and having a shape for being removably positioned within a calibration port of said spectrometer, said structure including a first layered structural portion that simulates the human stratum corneum and a second layered structural portion that simulates the human epidermis, said structure being impregnated with an amount of glucose, said amount of glucose being representative of a blood-sugar level value of a diabetic person, said value being used for calibrating said spectrometer.

2. A calibration standard apparatus as described in claim 1, wherein said apparatus further comprises:

a portion having embedded coded information.

3. A calibration standard apparatus as described in claim 2, wherein:

said embedded coded information comprises a bar code portion, a resistor code, a semiconductor memory device, and a reserved space for future coded features.

4. A calibration standard apparatus as described in claim 2, wherein said apparatus further comprises:

a handling portion.

5. A calibration standard apparatus as described in claim 4, wherein said embedded coded information comprises a bar code portion, a resistor code, a semiconductor memory device, and a reserved space for future coded features.

6. A calibration standard apparatus as described in claim 1, wherein said shape comprises a rectangular solid, and wherein said first layered structural portion comprises a side intended for being placed in contact with an optical window of said spectrometer and being exposed to the spectrometer's thermal mass to effect thermal gradients on said standard.

7. A calibration standard apparatus as described in claim 1, wherein
said shape comprises a cylindrical body and wherein said first layered structural portion comprises a side intended for being placed in contact with an optical window of said spectrometer and being exposed to the spectrometer's thermal mass to effect thermal gradients on said standard.

8. A calibration standard apparatus as described in claim 1, wherein
said blood-sugar level value comprises a concentration of glucose selected from a group of glucose concentration values comprising 0%, 50, 100, 500, 1000 mg/dl of glucose.

9. A calibration standard apparatus as described in claim 8, wherein
a group of said calibration said standard apparatus are provided, said group of standards comprising respective calibration standards having 0%, 50, 100, 500, 1000 mg/dl of glucose, said group of standards being packaged in a hermetic container and treated to prolong shelf life and to retard microbial growth, said container being provided with identifying information corresponding to said packaged group of standards.

10. A calibration standard apparatus as described in claim 9, wherein
said group of standards are provided as sterile calibration standards.

11. A calibration standard apparatus as described in claim 1, wherein said first layered structural portion comprises the following properties:
a thickness=50 μm+/−20 μm;
a moisture content less than 20%;
a no spectral features in the infrared band from 3–12 μm;
a thermal conductivity in the range of 0.21 to 0.26 watts/meter-° C., and
a specific heat in the range of 3578 to 3600 Joules/Kg-° C.

12. A calibration standard apparatus as described in claim 1, wherein said first layered structural portion comprises the following properties:
a thickness=300 μm+/−50 μm;
a moisture content=80% +/−10%;
a glucose spectral features at 9.6 μm;
a no other spectral features in the infrared band from 3–12 μm;
a thermal impedance in the range of 0.3 to 0.52 watts/meter-° C., and
a specific heat in the range of 3200 to 3400 Joules/Kg-° C.

13. A diabetic blood-sugar level testing kit, comprising:
a non-invasive thermal gradient spectrometer; and
at least one calibration standard apparatus for use in calibrating said non-invasive thermal gradient spectrometer, said calibration standard apparatus comprising:
a layered polymeric standard having a structure that simulates human skin, said structure being flat and having a shape for being removably positioned within a calibration port of said spectrometer, said structure including a first layered structural portion that simulates the human stratum corneum and a second layered structured portion that simulates the human epidermis, said structure being impregnated with an amount of glucose, said amount of glucose being representative of a blood-sugar level value of a diabetic person, said value being used for calibrating said spectrometer.

14. A diabetic blood-sugar level testing kit as described in claim 13, wherein:
said non-invasive thermal gradient spectrometer comprises a display portion having a plurality of window areas for displaying information about operational activity of said spectrometer, said activity including displaying standard concentration value, displaying actual concentration readout, and displaying message of calibration results and suggested action.

15. A diabetic blood-sugar level testing kit as described in claim 14, wherein:
said spectrometer comprises a remote network communication port and internal circuitry coupled to said remote network communication port for effecting remote calibration of said spectrometer by a remote computer and for accessing a remote database comprising patient information including treatment options in accordance with a patients history of blood-sugar readings.

16. A method of calibrating a thermal gradient spectrometer, said method comprising the steps of:
a) providing a diabetic blood-sugar level testing kit, said kit comprising:
a non-invasive thermal gradient spectrometer, said non-invasive thermal gradient spectrometer comprising:
a display portion having a plurality of window areas for displaying information about operational activity of said spectrometer, said activity including displaying standard concentration value, displaying actual concentration readout, and displaying message of calibration results and suggested action; and
a remote network communication port and internal circuitry coupled to said remote network communication port for effecting remote calibration of said spectrometer by a remote computer and for accessing a remote database comprising patient information including treatment options in accordance with a patient's history of blood-sugar readings; and
at least one calibration standard apparatus for use in calibrating said non-invasive thermal gradient spectrometer, said calibration standard apparatus comprising:
a layered polymeric standard having a structure that simulates human skin, said structure being flat and having a shape for being removably positioned within a calibration port of said spectrometer, said structure including a first layered structural portion that simulates the human stratum corneum and a second layered structural portion that simulates the human epidermis, said structure being impregnated with an amount of glucose, said amount of glucose being representative of a blood-sugar level value of a diabetic person, said value being used for calibrating said spectrometer (b) placing said spectrometer in a calibration mode;
(c) placing said standard apparatus in said communications port;
(d) exposing said positioned standard in step (c) to thermal gradients from a thermal mass window in said spectrometer;
(e) scanning said standard exposed to said thermal gradient;

(f) determining a glucose concentration of said scanned standard;

(g) comparing said determined glucose concentration against an actual glucose concentration impregnated in said standard;

(h) determining a type of calibration action to be taken; and (i) displaying results of said calibration taken.

17. A method of calibrating a thermal gradient spectrometer, as described in claim 16, wherein said step (h) comprises a local self-adjusting calibration step.

18. A method of calibrating a thermal gradient spectrometer, as described in claim 16, wherein said step (h) comprises a remote calibrating step.

19. A method of calibrating a thermal gradient spectrometer, as described in claim 16, wherein said step (i) comprises an "adjustment complete" message.

20. A method of calibrating a thermal gradient spectrometer, as described in claim 16, wherein said step (i) comprises a "perform manual adjustments" message.

* * * * *

UNITED STATES PATENT AND TRADEMARK OFFICE
CERTIFICATE OF CORRECTION

PATENT NO.   : 6,196,046 B1                                      Page 1 of 1
DATED        : March 6, 2001
INVENTOR(S)  : James R. Braig It is certified that error appears in the above-identified patent and that said Letters Patent is hereby corrected as shown below:

Column 1,
Line 21, after the word "are" delete [force] and replace with -- forced --.
Line 51, after the word "or" delete [a periodic] and replace with -- aperiodic --.

Column 4,
Line 12, after the word "certain" add -- patient --.
Line 38, after the word "If" delete [not] and replace with -- no --.

Column 7,
Line 17, after the word "calibration" delete [said].
Line 33, after "20%" add -- by weight --.
Line 34, delete the first word [a].
Line 35, after the word "thermal" delete [conductivity] and replace with -- impedance --.
Line 45, delete the first word [a].

Signed and Sealed this

Fourteenth Day of August, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,196,046 B1
DATED : March 6, 2001
INVENTOR(S) : James R. Braig, Bernhard B. Sterling, Daniel S. Goldberger, Joan C. Godfrey, Kamrava Azizi, David J. Correia and Charles E. Kramer It is certified that error appears in the above-identified patent and that said Letters Patent is hereby corrected as shown below:

Column 7, claim 12,
Line 41, after the word "said" delete the word [first] replace with -- second --.

Column 8, claim 16,
Line 61, after the word "said" delete the word [communications] replace with -- input --.

Signed and Sealed this

Twentieth Day of November, 2001

*Attest:*

*Attesting Officer*

NICHOLAS P. GODICI
*Acting Director of the United States Patent and Trademark Office*